US012420054B1

United States Patent
Fang

(10) Patent No.: US 12,420,054 B1
(45) Date of Patent: Sep. 23, 2025

(54) ROTARY SPRAY RING AROMATHERAPY HUMIDIFIER

(71) Applicant: Limei Fang, Ganzhou (CN)

(72) Inventor: Limei Fang, Ganzhou (CN)

( * ) Notice: Subject to any disclaimer, the term of this patent is extended or adjusted under 35 U.S.C. 154(b) by 0 days.

(21) Appl. No.: 19/010,646

(22) Filed: Jan. 6, 2025

(30) Foreign Application Priority Data

Mar. 19, 2024 (CN) .......................... 202420530033.6

(51) Int. Cl.
*A61M 21/02* (2006.01)
*B05B 7/26* (2006.01)

(52) U.S. Cl.
CPC .............. *A61M 21/02* (2013.01); *B05B 7/26* (2013.01)

(58) Field of Classification Search
CPC ... A61M 21/02; B05B 7/26; F24F 6/00; F24F 6/12; F24F 2006/003; A61L 2209/10
USPC ................................ 239/590, 17; 261/119.1
See application file for complete search history.

(56) References Cited

U.S. PATENT DOCUMENTS

| | | | | |
|---|---|---|---|---|
| 7,441,756 B2* | 10/2008 | Niedermann | ............. | F24F 6/00 |
| | | | | 261/DIG. 65 |
| 8,025,270 B2* | 9/2011 | Hou | ........................ | F24F 6/12 |
| | | | | 261/78.2 |
| 8,146,892 B2* | 4/2012 | Hou | ........................ | F24F 6/00 |
| | | | | 239/23 |
| 9,151,509 B2* | 10/2015 | Hou | ........................ | F24F 6/02 |
| 12,161,783 B1* | 12/2024 | Fang | ........................ | F24F 6/16 |
| 2009/0250529 A1* | 10/2009 | Hou | ........................ | F24F 6/02 |
| | | | | 239/23 |
| 2013/0154131 A1* | 6/2013 | Hou | ..................... | B01F 23/213 |
| | | | | 261/24 |
| 2015/0008599 A1* | 1/2015 | Hou | ........................ | F24F 6/12 |
| | | | | 261/127 |
| 2023/0125562 A1* | 4/2023 | Yang | ........................ | A61L 9/01 |
| | | | | 362/311.01 |

FOREIGN PATENT DOCUMENTS

| | | |
|---|---|---|
| CN | 217540950 U | 10/2022 |
| CN | 218763784 U | 3/2023 |
| CN | 220707596 U | 4/2024 |

* cited by examiner

*Primary Examiner* — Joseph A Greenlund
*Assistant Examiner* — Kevin Edward Schwartz
(74) *Attorney, Agent, or Firm* — Nitin Kaushik

(57) ABSTRACT

A rotary spray ring aromatherapy humidifier comprising a water tank is provided. An atomizing module and two power take-offs (PTOs) are fixedly arranged below the water tank; a driving gear and a fan blade are installed on the two PTOs, respectively; the driving gear and the fan blade are located inside the water tank; an intermediate frame is covered above the water tank; air vents, ring-spraying holes, and at least one through-hole are arranged on the intermediate frame; a limiting component is constructed below ring-spraying holes; and a rotatable transmission gear is arranged outside the limiting component; a gear tray is arranged below the intermediate frame; and a gear escape hole through which the transmission gear passes is formed in the gear tray. The present disclosure has the following beneficial effects: The product is designed with decorative parts that are arranged in a rotary manner.

6 Claims, 12 Drawing Sheets

11-1

11-2

12-1

12-2

ROTARY SPRAY RING AROMATHERAPY HUMIDIFIER

CROSS-REFERENCE TO RELATED APPLICATIONS

The application claims priority to Chinese patent application No. 2024205300336, filed on Mar. 19, 2024, the entire contents of which are incorporated herein by reference.

TECHNICAL FIELD

The present disclosure belongs to the field of aromatherapy diffusers, in particular to a rotary spray ring aromatherapy humidifier.

BACKGROUND

The mist-spraying mode and display effect of the existing aromatherapy humidifiers are relatively single. Most aromatherapy diffusers simply atomize water and spray its mist to the outside, so the display effect is relatively single. Moreover, most aromatherapy diffusers have simple display effects, making them less attractive and ornamental. This utility model presents an aromatherapy humidifier that is more ornamental in terms of structure and mist-emitting mode.

SUMMARY

In view of this, the present disclosure provides a rotary spray ring aromatherapy humidifier.

To achieve the above purpose, the following technical solution is adopted in the present disclosure. It comprises a water tank, wherein an atomizing module and two power take-offs (PTOs) are fixedly arranged below the water tank; a driving gear and a fan blade are installed on the drive ends of the two PTOs, respectively; and the driving gear and the fan blade are located inside the water tank;
  an intermediate frame is covered above the water tank;
  the intermediate frame is provided with air vents, ring-spraying holes, and at least one through-hole; a limiting component is constructed below the ring-spraying holes;
  an outer side of the limiting component is provided with a rotatable transmission gear, and a gear tray is installed below the intermediate frame; and
  the gear tray is provided with a gear escape hole through which the transmission gear passes; a rotatably driven gear corresponding to the through-hole is arranged between the gear tray and the intermediate frame, and rotary decorative parts are fixedly arranged above the driven gear.

Further, an air guide frame is arranged between the air vents on the intermediate frame.

Further, second interconnecting holes that are communicated with the air vents are arranged on the gear tray, and an air guide frame is arranged between the second interconnecting holes.

Further, a diameter of the limiting component is larger than that of the fan blade, and the fan blade is arranged at the inner hole of the limiting component.

Further, an air duct is arranged on a periphery of the fan blade and is fixedly connected to a lower part of the intermediate frame or the gear tray.

Further, the water tank is constructed with two upwardly protruding accommodations, and the PTOs are installed inside the holding chamber.

Further, the transmission gear is configured with a first transmission tooth meshing with the driving gear and a second transmission tooth meshing with the driven gear.

Further, a diameter of a second transmission tooth is larger than that of the gear escape hole, and a second transmission tooth abuts above the gear escape hole.

Further, a bearing is arranged between an inner side of the transmission gear and the limiting component.

Further, the driving gear, the transmission gear, and the driven gear are engaged for transmission; when the driven gear rotates, it drives the rotary decorative parts to rotate together; and the rotary decorative parts are arranged on the intermediate frame in a ring shape, and the ring-spraying holes are arranged in the middle of several rotary decorative parts.

Compared with the prior art, the rotary spray ring aromatherapy humidifier provided by the present disclosure has the following advantages:
1. The product of the present disclosure is designed with decorative parts arranged in rotation, and the aromatherapy humidifier can also produce a mist ring spraying effect, which has better visual effects than traditional aromatherapy humidifiers.
2. The present disclosure can also realize the switching of two mist-emitting modes, i.e., mist ring spraying and mist column spraying, thus providing a better use experience.

BRIEF DESCRIPTION OF DRAWINGS

To illustrate more clearly technical solutions in embodiments of the present disclosure, drawings to be used to describe the embodiments or prior art are introduced briefly below. Apparently, the drawings described below are only some embodiments of the present disclosure, and persons of ordinary skill in the art can derive other drawings from these drawings without creative efforts.

The reference symbols in the figures are as follows.

Figure 1:
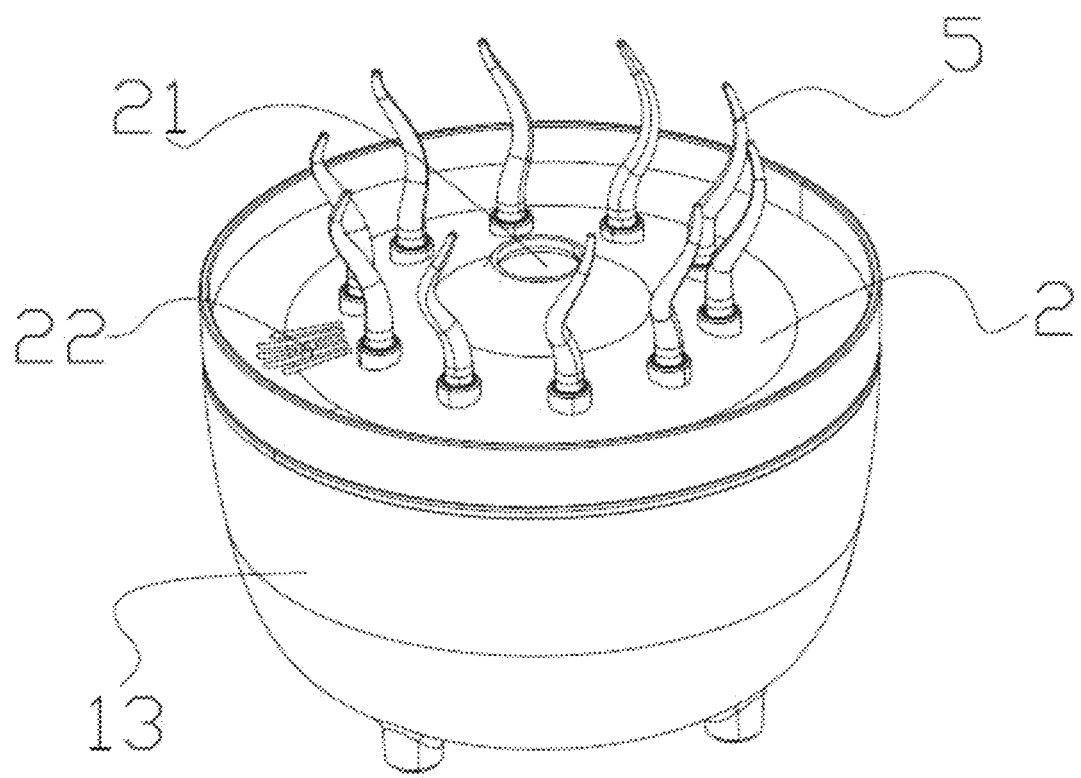
FIG. 1 is a schematic diagram of the overall structure of Embodiment I according to the present disclosure.

| Designation | No. | Designation | No. | Designation | No. |
|---|---|---|---|---|---|
| Water tank | 1 | Atomizing module | 11 | Control circuit board | 12 |
| Bottom case | 13 | First PTO | 14 | Second PTO | 15 |
| Intermediate frame | 2 | Ring-spraying holes | 21 | Air vents | 22 |
| Through-hole | 23 | Limiting component | 24 | | |
| Driving gear | 3 | Transmission gear | 31 | First transmission tooth | 311 |
| Second transmission tooth | 312 | Driven gear | 32 | | |
| Gear tray | 4 | First interconnecting hole | 41 | Second interconnecting hole | 42 |
| Gear escape hole | 43 | Air duct | 44 | Holding chamber | 7 |
| Rotary decorative parts | 5 | Fan blade | 6 | Air guide frame | 8 |

DETAILED DESCRIPTION OF THE EMBODIMENTS

To better understand the technical solution of the present disclosure, the embodiments provided by the present disclosure are described in detail below with reference to the drawings.

The above is a detailed introduction to the rotary spray ring aromatherapy humidifier provided by the embodiments according to the present disclosure. For persons of ordinary skill in the art, there may be changes in specific implementation methods and application scope according to the idea of the embodiments of the present disclosure. To sum up, the contents of the Specification shall not be construed as limiting the present disclosure.

It should be understood that in the description of the present disclosure terms indicating the directions or position relationships such as "length", "width", "upper", "lower", "middle", "front", "rear", "left", "right", "vertical", "horizontal", "top", "bottom", "inside" and "outside" are based on those shown in the drawings. They are used only for facilitating the description of the present disclosure and simplifying the description, not for indicating or implying that the target devices or elements must have a special direction and be constructed and operated in the special direction. Therefore, they cannot be understood as the restrictions to the present disclosure.

In the present disclosure, the terms "installation", "connection with", "connection to", and "attachment to" shall be understood in a general sense. For example, they can be understood as fixation, attachment, or connection. They may be mechanically or electrically connected. They can be direct or indirect connections through intermediate media and can be the connection between two elements. Persons of ordinary skill in the art can understand the specific meanings of the above terms in the present disclosure as appropriate.

As shown in FIGS. 1-12, the embodiments of the present disclosure provide a rotary spray ring aromatherapy humidifier.

Figure 2:
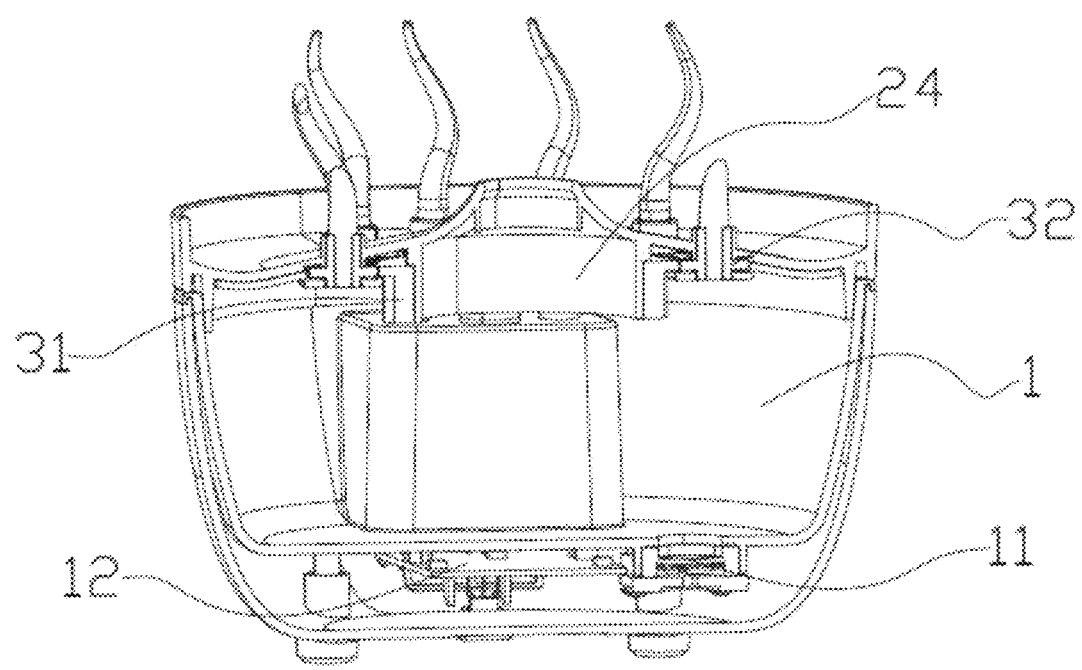
FIG. 2 is a sectional view of the overall structure of Embodiment I according to the present disclosure.
Figure 7:
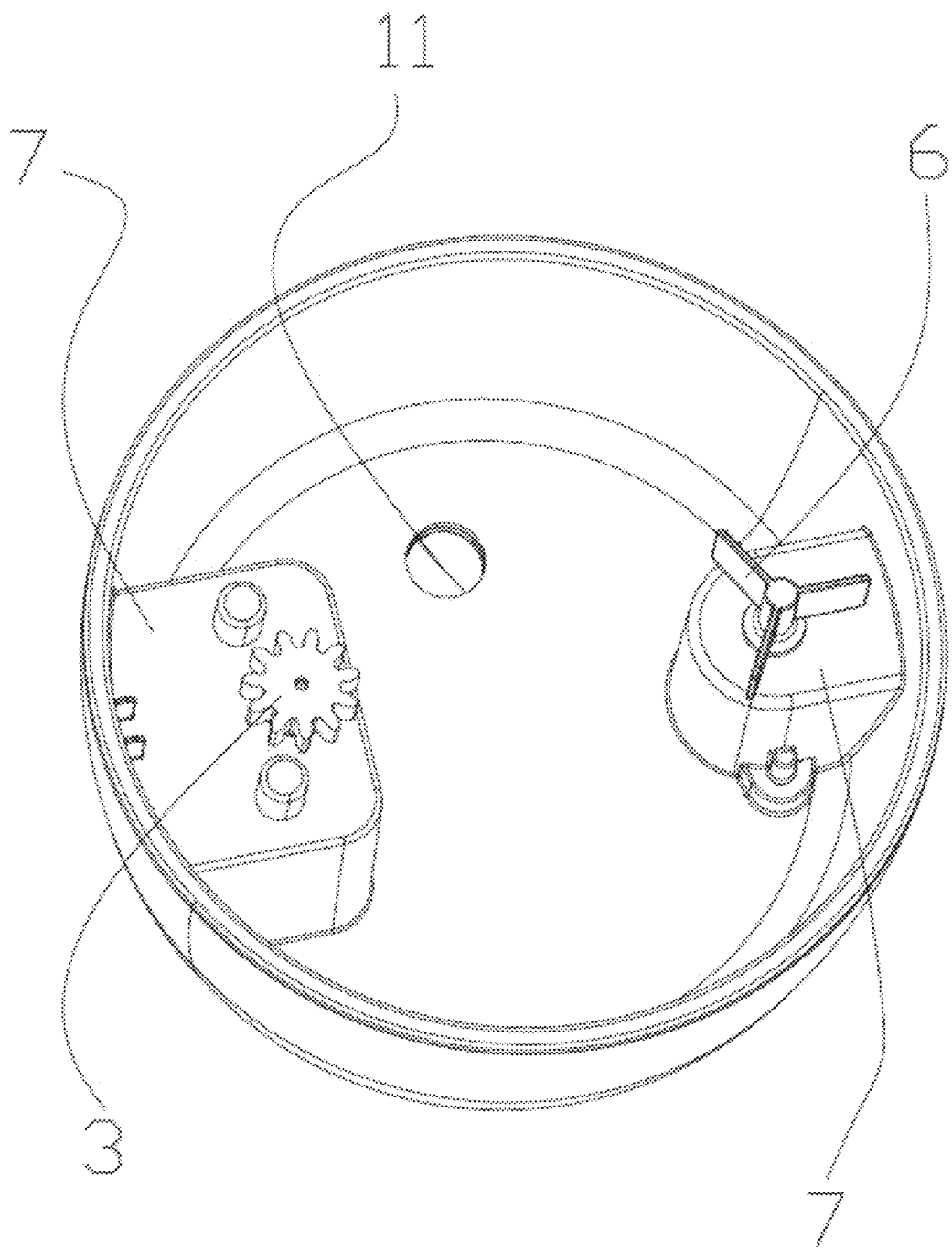
FIG. 7 is a schematic diagram of the structure of the water tank of Embodiment I according to the present disclosure.

As shown in FIGS. 1-2, the present disclosure comprises a water tank 1, a bottom case 13, and an intermediate frame 2. When the water tank 1 is fixed above the bottom case 13, related components such as a control circuit board 12, buttons, and PTOs are fixed in an area enclosed between the bottom case 13 and the water tank 1. The related electronic components are electrically connected to the control circuit board and controlled by buttons or remote controllers. This technology is a well-known attempt in this field and will not be described here again. As shown in FIG. 7, the bottom of the water tank 1 is provided with a PTO holding chamber 7, the holding chamber 7 protrudes from the water tank, and the PTOs are fixedly installed in the holding chamber 7. The bottom of the water tank 1 is provided with an atomizing hole, and an atomizing module 11 is fixedly arranged below the atomizing hole to atomize the water inside water tank 1.

The opening of a water tank 1 is covered with an intermediate frame 2, and the intermediate frame 2 is provided with ring-spraying holes 21, air vents 22, and through-holes 23 communicating with the water tank 1; in this embodiment, the ring-spraying holes 21 are arranged on an inner side of several rotary decorative parts 5; a limiting component 24 is arranged below ring-spraying holes 21; an upper part of the limiting component 24 is fixedly connected to a lower part of ring-spraying holes 21 of the intermediate frame 2, and a lower part of the limiting component 24 is arranged in an open shape; and a transmission gear 31 is rotatably sleeved on an outer side of the limiting component 24.

Figure 3:
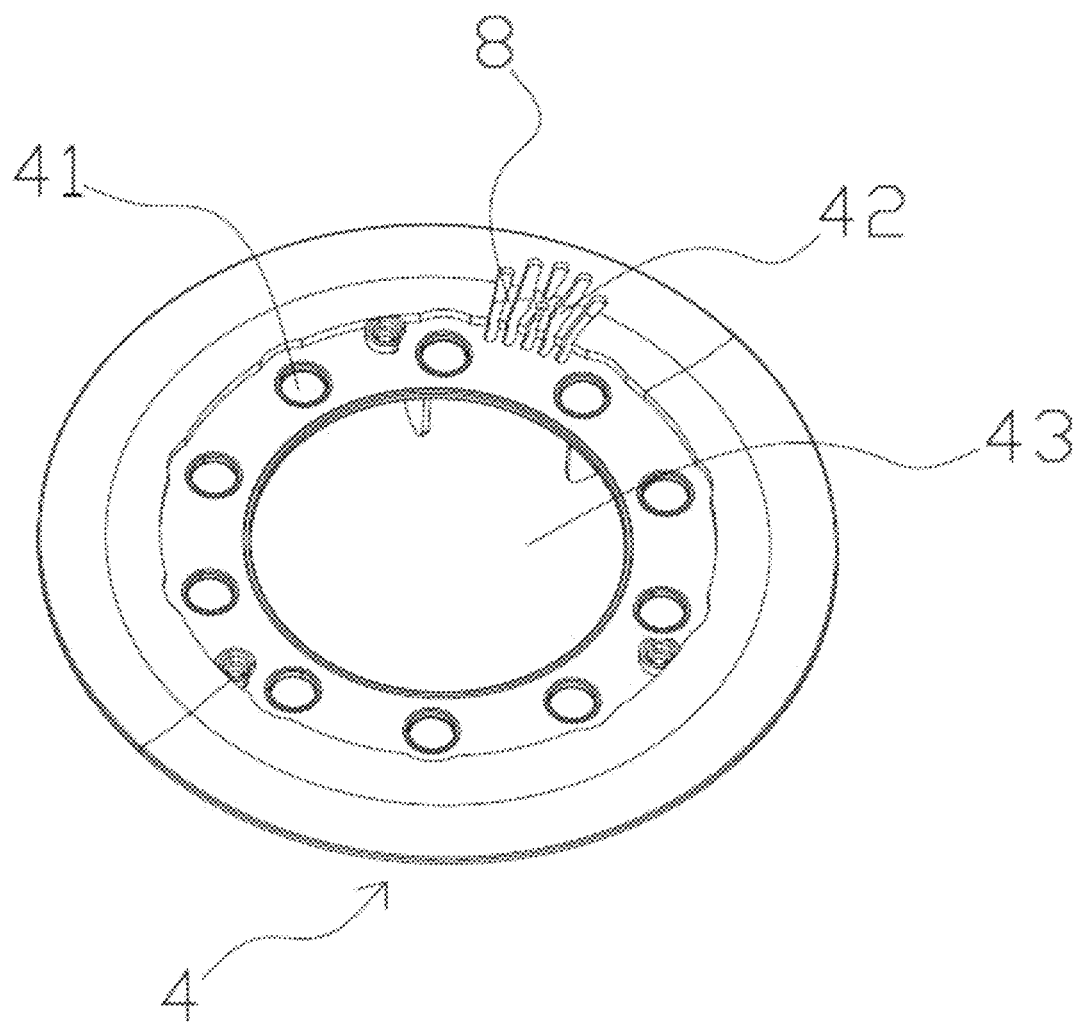
FIG. 3 is a schematic diagram of the structure of the gear tray of Embodiment I according to the present disclosure.
Figure 4:
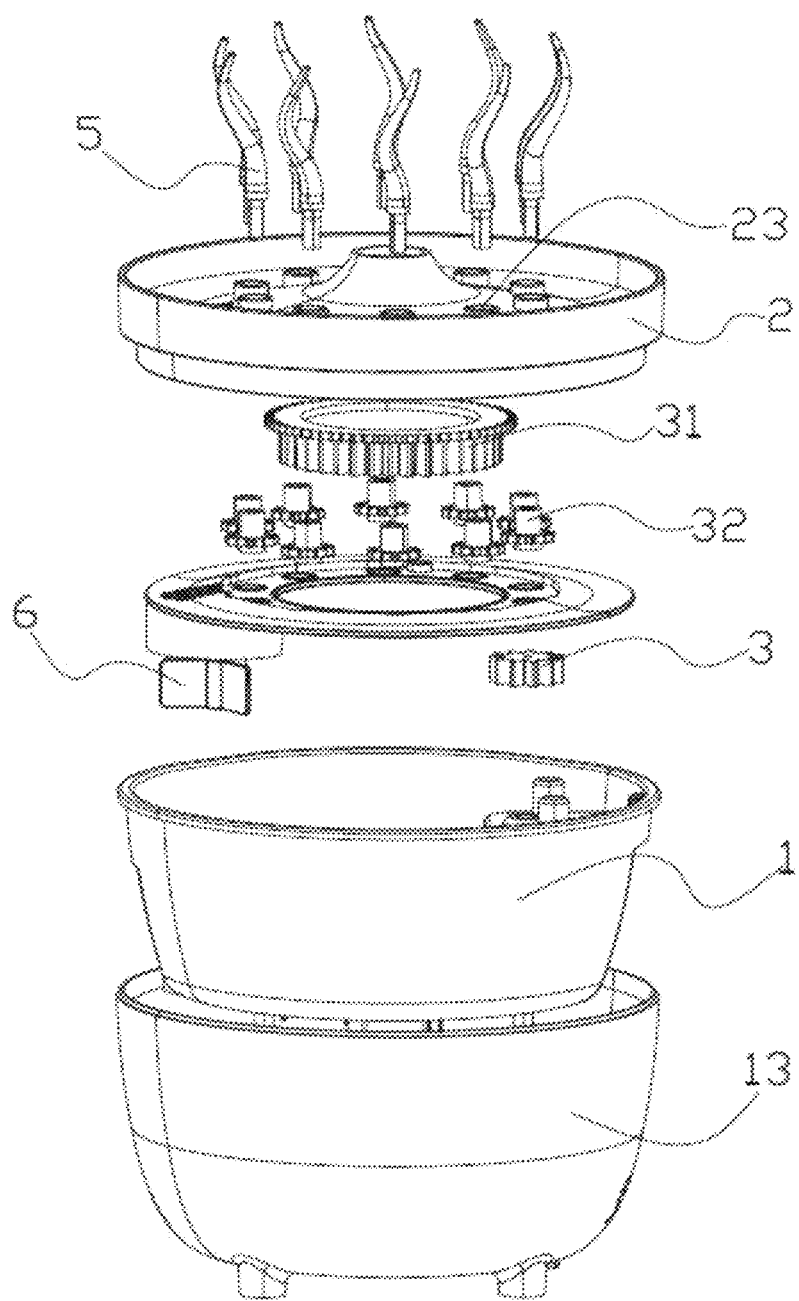
FIG. 4 is a schematic diagram of the exploded structure of Embodiment I according to the present disclosure.

As shown in FIGS. 3-4, a gear tray 4 is arranged below the intermediate frame 2, and the gear tray 4 is detachably arranged below the intermediate frame 2. Specifically, the gear tray 4 may be arranged below the intermediate frame 2 by bolting, clamping or other means. The gear tray 4 is provided with first interconnecting holes 41, the first interconnecting holes 41 correspond to the through-holes 23. A gear escape hole 43 for the transmission gear 31 and the limiting component 24 to pass is further provided in the middle of the gear tray 4. After the transmission gear 31 passes through the gear escape hole 43, it meshes with the driven gear 32 above the gear tray 4.

When the gear tray 4 is fixed below the intermediate frame 2, the driven gear 32 is limited by the gear tray 4 and the intermediate frame 2 so that the driven gear 32 can be rotatably fixed between the gear tray 4 and the intermediate frame 2. The driven gear 32 is aligned with through-holes 23 formed on the intermediate frame 2, an bottom end of the rotary decorative parts 5 is disposed at through-holes 23, and the bottom end of the rotary decorative parts 5 is fixedly connected to the driven gear 32. When the driven gear 32 rotates, it will drive the rotary decorative parts 5 to rotate. In this embodiment, the rotary decorative parts 5 can be connected above the driven gear by means of clamping, screwing, and integral connection, which all belong to the protection scope of the present disclosure. Several rotary decorative parts 5 are arranged above the intermediate frame 2 at equal intervals, and ring-spraying holes 21 are disposed inside the several rotary decorative parts 5.

The transmission gear 31 is divided into a second transmission tooth 312 meshed with the driven gear 32 and a first transmission tooth 311 meshed with the driving gear 3, and a diameter of the second transmission tooth 312 is larger than those of the first transmission tooth 311 and the gear escape hole 43. After the transmission gear 31 is installed on the limiting 24, a lower portion of the second transmission tooth 312 abuts against an upper portion of the gear escape hole 43 of the gear tray 4, so that the gear tray 4 longitudinally supports the transmission gear 31 to prevent the transmission gear 31 from falling off at the gear escape hole 43. In addition, in this embodiment, the inner side of the transmission gear 31 is rotatably arranged on the outer side of the limiting component 24, and the limiting component 24 plays a role of laterally limiting the transmission gear 31 to avoid lateral displacement of the transmission gear 31 and ensure that the transmission gear 31 rotates around the limiting component 24.

Figure 5:
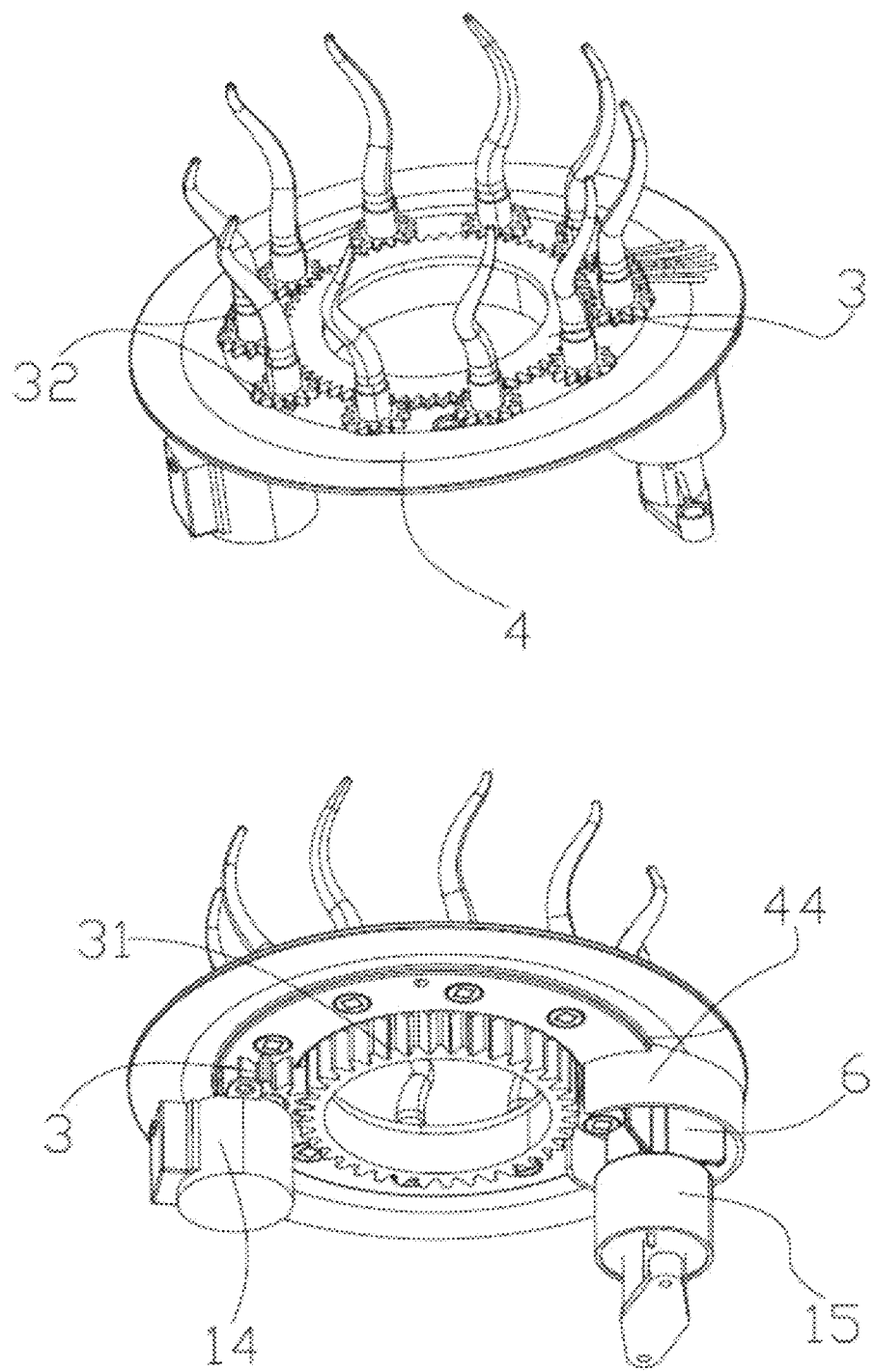
FIG. 5 is a schematic diagram of the structure of the gear tray of Embodiment I according to the present disclosure.
Figure 6:
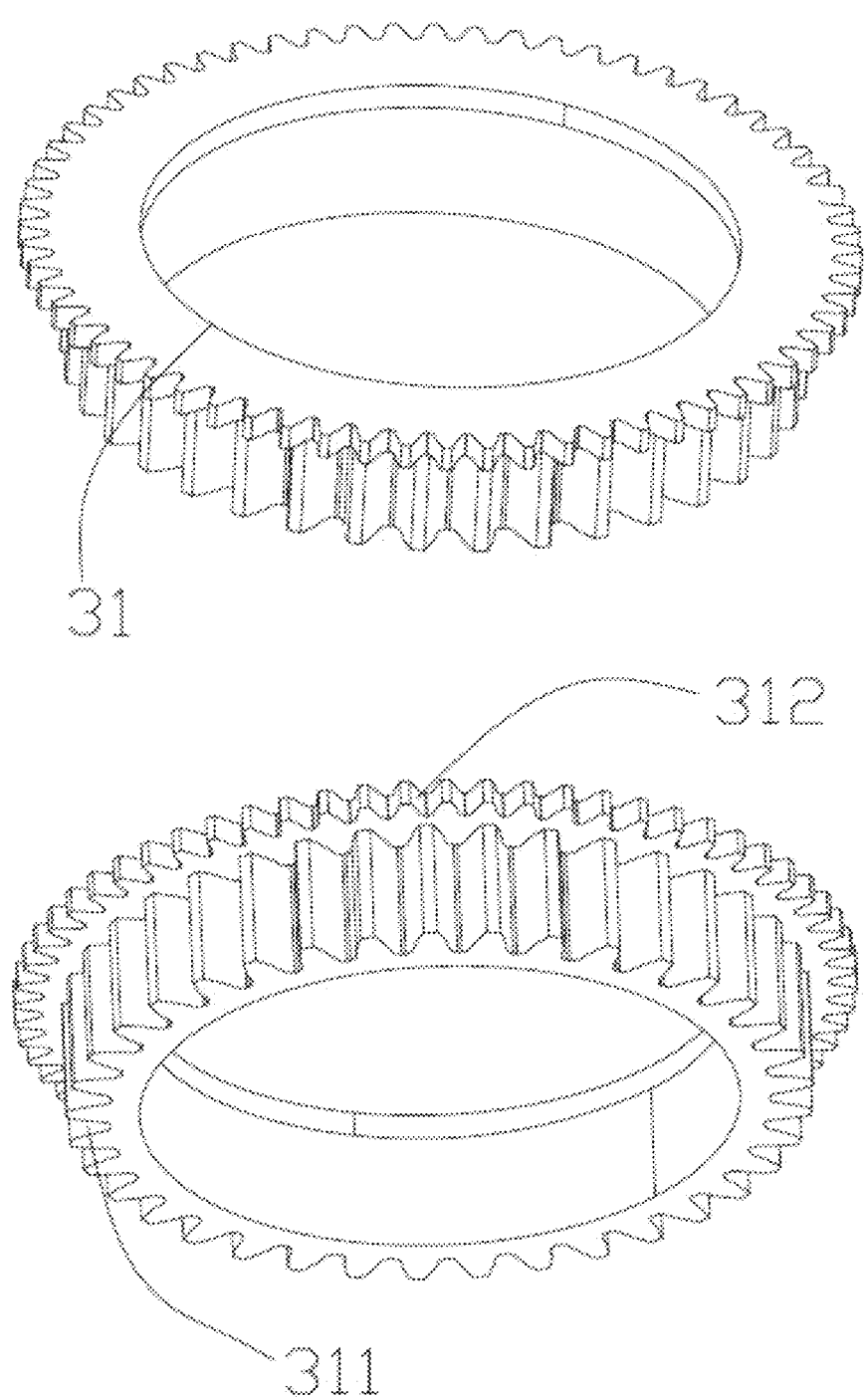
FIG. 6 is a schematic diagram of the structure of the transmission gear of Embodiment I according to the present disclosure.

As shown in FIGS. 5-6, two PTOs are arranged between the water tank 1 and the bottom case 13, namely a first PTO 14 and a second PTO 15. The drive shafts of the two PTOs extend into the water tank 1. The driving gear 3 is arranged on the drive shaft of the first PTO 14. When the first PTO 14 is running, it will drive the driving gear 3 to rotate. The driving gear 3 will drive the transmission gear 31 to rotate. When the transmission gear 31 rotates, it will drive the driven gear 32 at its outer side to rotate. Since rotary decorative parts 5 are fixedly arranged above the driven gear 32, the rotary decorative parts 5 finally rotate.

The second PTO 15 is arranged below the air vents 22, and a fan blade 6 is arranged on a drive shaft of the second PTO 15; by driving the fan blade 6 to rotate, two mist-emitting effects of mist column spraying and mist ring spraying of ring-spraying holes 21 can be achieved. In this embodiment, the gear tray 4 is provided with the second interconnecting holes 42 that are communicated with the air vents 22 to improve the air intake effect of the air vents 22. An annular air duct 44 is fixedly arranged below the gear tray 4, and the fan blade 6 is arranged inside the annular air duct 44, so that the wind generated by the fan blade 6 will not be dispersed to both sides, thus improving the wind effect generated by the fan blade 6.

In other alternative embodiments, the second interconnecting holes 42 can be omitted; secondary interconnecting holes 42 are designed because the width of the gear tray 4 is too large and the gear tray 4 blocks the air outlet from the air vents 22; in other embodiments of the gear tray 4, the width of the gear tray 4 can be reduced so that the gear tray 4 will not block the air inlet and outlet from the air vents 22, and the air vents 22 are directly communicated with the water tank. In this embodiment, the annular air duct 44 may be fixedly arranged below the air vents 22 of the intermediate frame 2.

It is assumed that the fan blade 6 rotates forward to blow mist outward, and the fan blade 6 rotates reversely to blow air inward (in other alternative embodiments, the fan blade 6 can also rotate reversely to blow mist outward, and the fan blade 6 rotates forward to blow air inward, so it is only necessary to change the design specifications of the fan blade 6). As shown in 11-1 of FIG. 11, when the second PTO 15 drives the fan blade 6 to intermittently reverse, the fan blade 6 will intermittently blow air into the water tank 1, so that the mist inside water tank 1 is instantaneously pressurized and finally sprayed outward along ring-spraying holes 21 to form an annular mist ring at ring-spraying holes 21.

Figure 11:
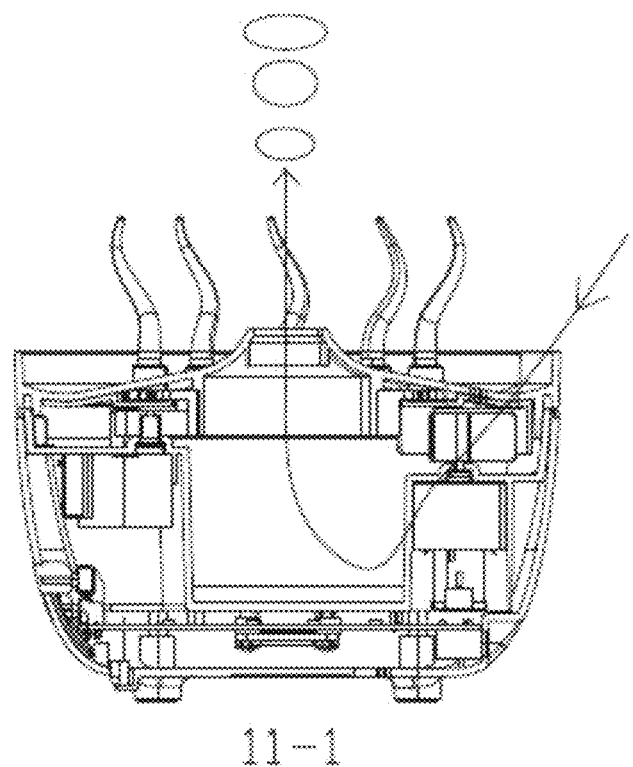
FIG. 11 is a schematic diagram of the mist-emitting mode of Embodiment I according to the present disclosure.
Figure 11:
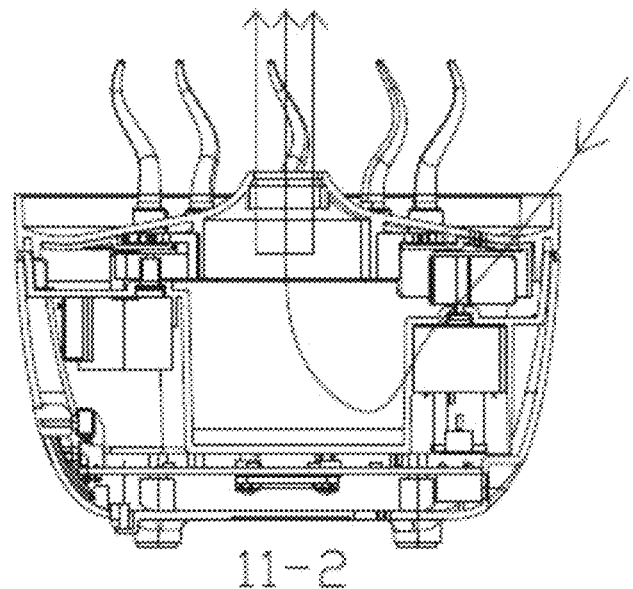

As shown in 11-2 of FIG. 11, when the fan blade 6 is continuously and intermittently reversed, an annular mist ring is continuously ejected from ring-spraying holes 21 to the outside. When the second PTO 15 drives the fan blade 6 to continuously reverse, the wind will be blown out from ring-spraying holes 21 to the outside and incidentally blow the mist out along ring-spraying holes 21 to the outside, so that a mist column is formed at ring-spraying holes 21 to form a unique visual effect.

In this embodiment, both the mist column spraying effect of the ring-spraying holes 21 and the mist ring spraying effect of the ring-spraying holes 21 are formed by blowing air to an inner side of the water tank 1 through the fan blade 6. At this moment, air vents 22 operate as air inlets, and ring-spraying holes 21 operate as air outlets.

Figure 8:
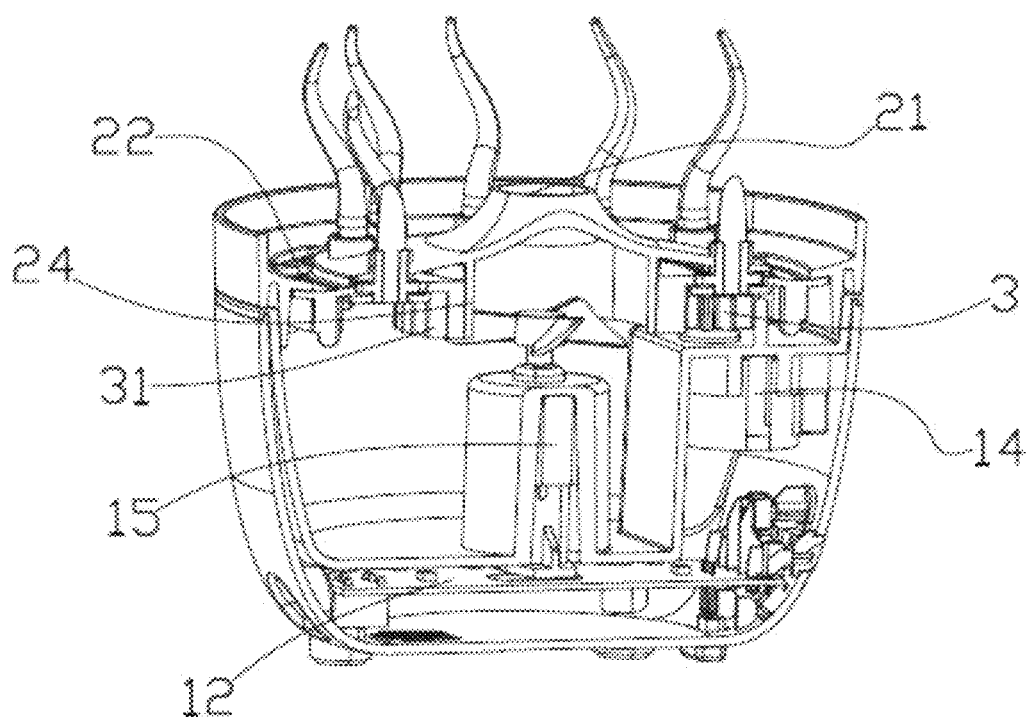
FIG. 8 is a sectional view of the overall structure of Embodiment II according to the present disclosure.
Figure 9:
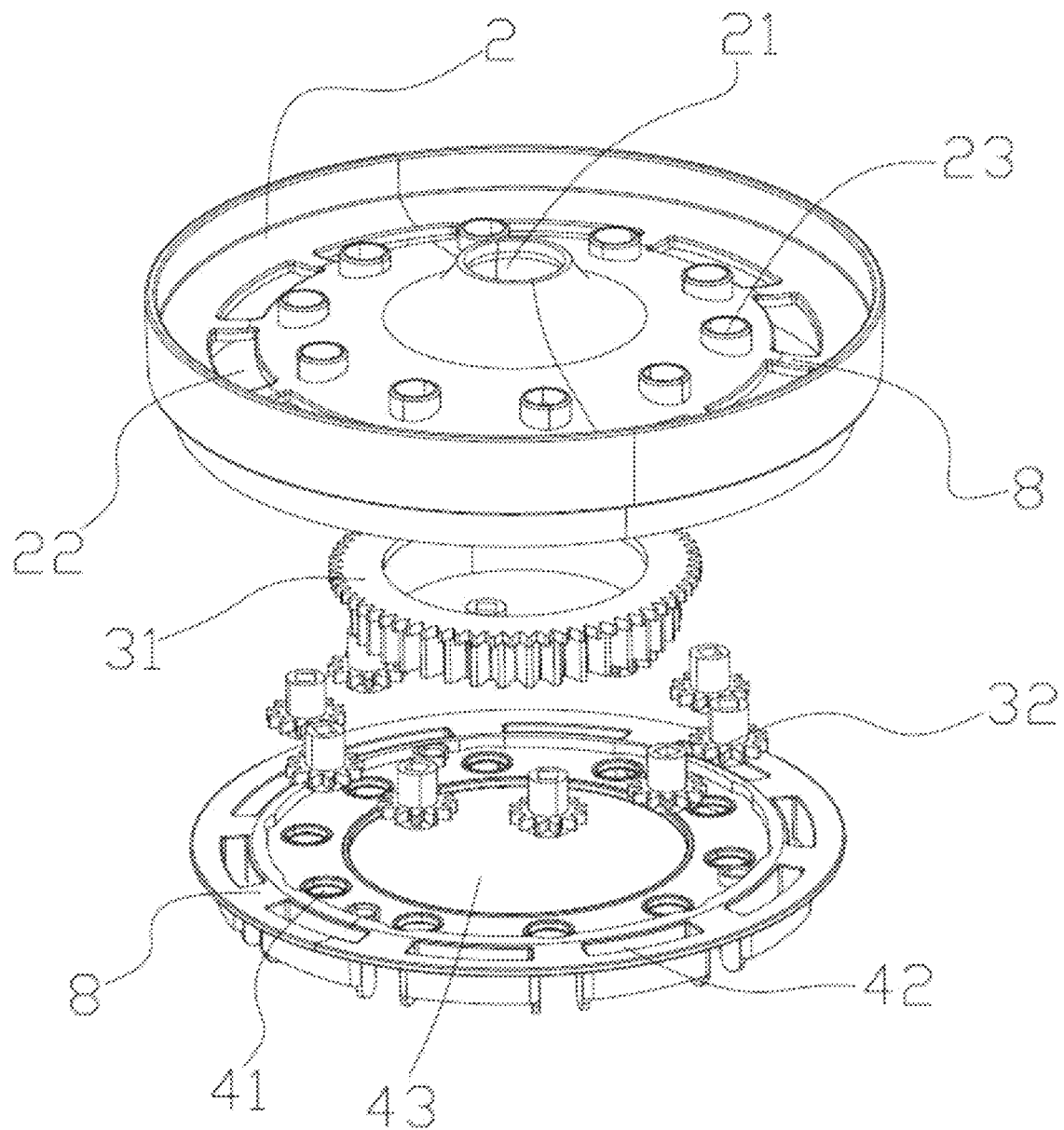
FIG. 9 is a schematic diagram of the exploded structure of Embodiment II according to the present disclosure.
Figure 10:
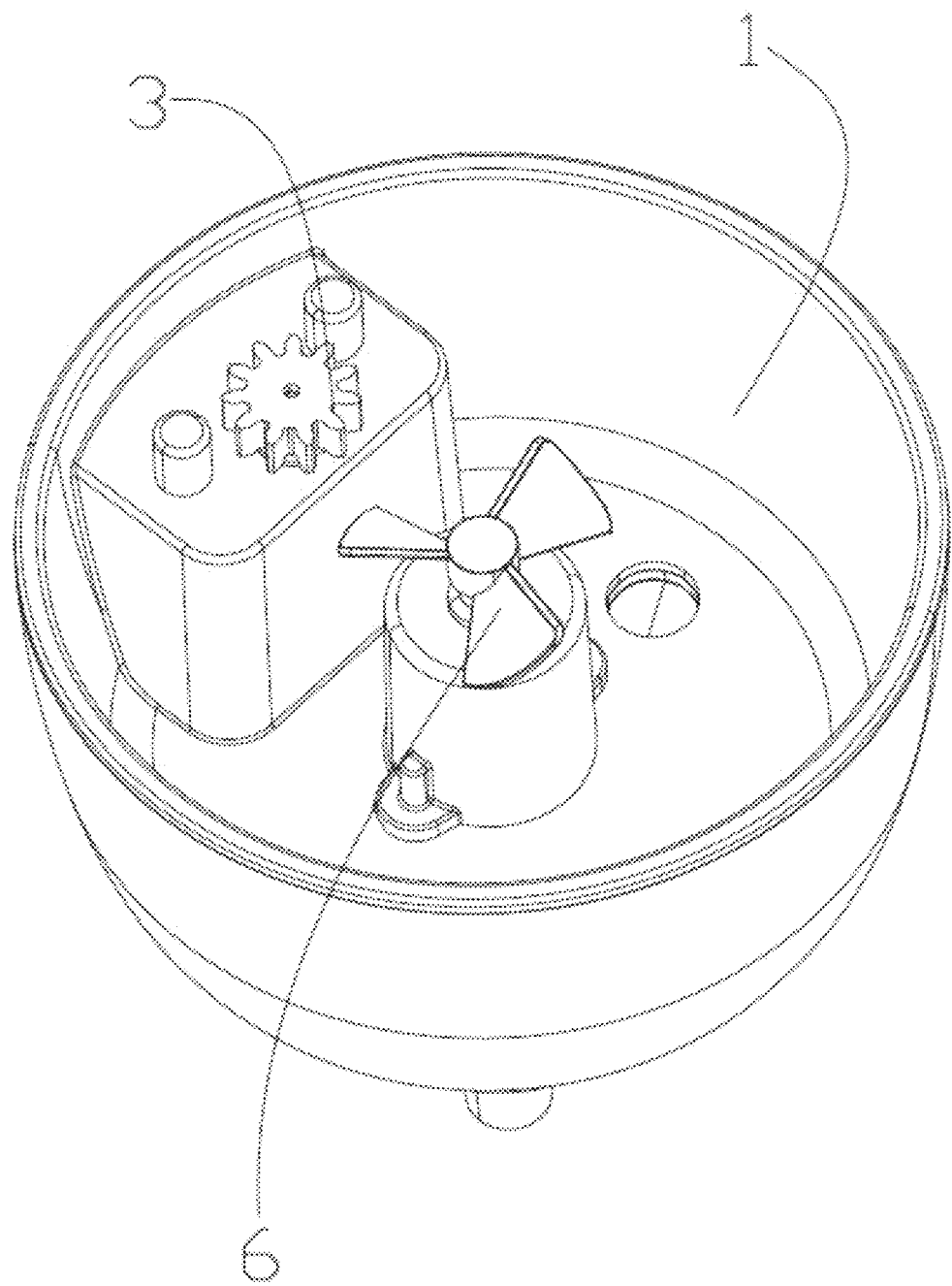
FIG. 10 is a schematic diagram of the structure of the water tank of Embodiment II according to the present disclosure.

As shown in FIGS. 8-9, in the second embodiment of the present disclosure, the rotating manner of rotary decorative parts 5 is consistent with that of the above-mentioned embodiments and will not be described again here. The difference lies in that at least one air vent 22 is arranged on the intermediate frame 2, air vents 22 are distributed above intermediate frame 2 in a ring shape, and ring-spraying holes 21 are arranged at an inner side of several air vents 22. Correspondingly, the gear tray 4 is provided with a plurality of second interconnecting holes 42 that are communicated with the air vents 22, and the second interconnecting holes 42 are distributed on the gear tray 4 in a ring shape.

To improve the mist-emitting effect, in the first and second embodiments, an air guide frame 8 is arranged at the second interconnecting holes 42 and the air vents 22. The air guide frame 8 ensures that the mist will not become disordered when the second interconnecting holes 42 and the air vents 22 emit mist, and the mist is sprayed outward as a whole regularly. The difference from the previous embodiment lies in that the fan blade 6 of the second PTO 15 is arranged at the inner hole of the limiting component 24 below ring-spraying holes 21. The second PTO 15 rotates the fan blade 6 so that ring-spraying holes 21 can spray mist rings to the outer side and the air vents 22 will spray mist columns to the outer side. The specific operation process is as follows;

It is assumed that the fan blade 6 rotates forward to blow mist outward, and the fan blade 6 rotates reversely to blow air inward (in other alternative embodiments, the fan blade 6 can also rotate reversely to blow mist outward, and the fan blade 6 rotates forward to blow air inward, so it is only necessary to change the specifications of the fan blade 6). A large amount of mist will be formed inside water tank 1 when the atomizing module 11 works, as shown in 12-1 of FIG. 12. When fan blade 6 rotates intermittently forward, the mist is intermittently and instantaneously ejected to the outside, so that an annular mist ring is instantaneously ejected from ring-spraying holes 21, forming a unique visual effect. When ring-spraying holes 21 eject annular mist rings to the outside, ring-spraying holes 21 act as air outlets while air vents 22 act as air inlets. When the fan blade 6 continuously rotates intermittently, ring-spraying holes 21 will continuously eject a mist ring to the outside.

Figure 12:
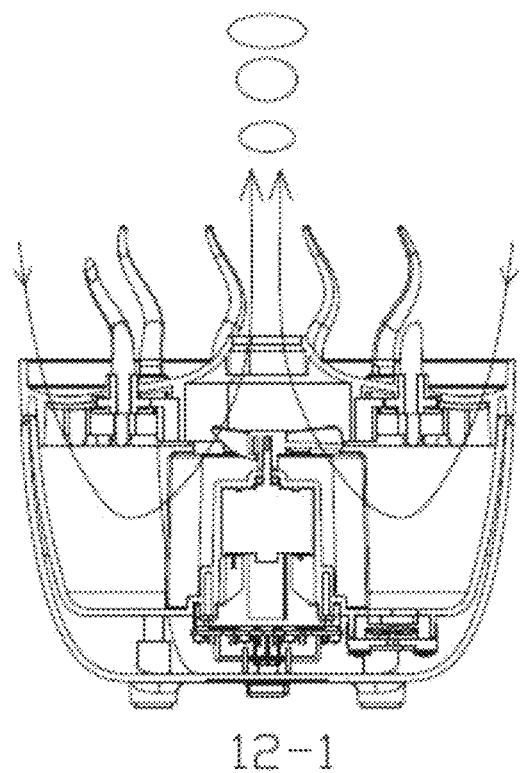
FIG. 12 is a schematic diagram of the mist-emitting mode of Embodiment II according to the present disclosure.
Figure 12:
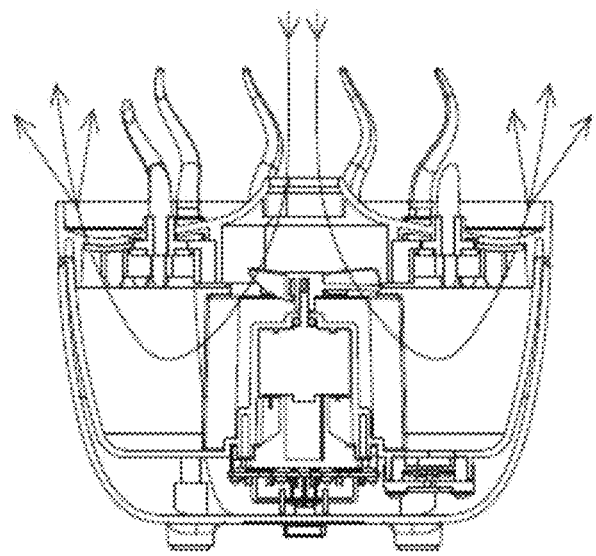

As shown in 12-2 of FIG. 12, when the fan blade 6 rotates reversely, the fan blade 6 will continuously rotate reversely, ring-spraying holes 21 operate as air inlets, and the air vents 22 operate as air outlets. Because there is mist inside water tank 1, when the fan blade 6 continues rotating reversely, the mist will be ejected from air vents 22 to form a unique mist column effect.

To improve the rotating smoothness of the transmission gear 31, a bearing (not shown in the figure) is arranged between the transmission gear 31 and the limiting component 24. The inner ring of the bearing is fixed on the limiting component 24, and the outer ring of the bearing is rotatably fixed on the transmission gear 31.

The description of various embodiments of the present disclosure is expressed for the illustrative purpose and is not aimed at limiting the disclosed embodiments. Many modifications and variations will be apparent to those having ordinary skill in the art without departing from the scope and spirit of the described embodiments. The terms used in the embodiments are intended to best explain the principles of the embodiments and their practical application or enable other persons having ordinary skill in the art to understand the embodiments disclosed herein. They shall not be construed as a limitation of the present disclosure.

What is claimed is:

1. A rotary spray ring aromatherapy humidifier comprising a water tank (1), atomizer (11) and two power take-offs (PTOs) fixedly arranged below the water tank (1); wherein a driving gear (3) and fan blade (6) are installed on a drive end of each of the two PTOs, respectively; and the driving gear (3) and fan blade (6) are located inside the water tank;

the rotary spray ring aromatherapy humidifier comprises an intermediate frame (2) that covers the water tank (1);

the intermediate frame (2) is provided with air vents (22), ring-spraying holes (21), and at least one through-hole (23); the rotary spray ring aromatherapy humidifier comprises a limiting plate (24) that is constructed below the ring-spraying holes (21);

an outer side of the limiting plate (24) is provided with a rotatable transmission gear (31), and the rotary spray ring aromatherapy humidifier comprises a gear tray (4) that is installed below the intermediate frame (2); and the gear tray (4) is provided with a gear escape hole (43) through which the transmission gear (31) passes; the rotary spray ring aromatherapy humidifier comprises a rotatably driven gear (32) corresponding to the at least one through-hole (23) that is arranged between the gear tray (4) and the intermediate frame (2), and the rotary spray ring aromatherapy humidifier also comprises rotary decorative parts (5) that are fixedly arranged above the driven gear (32).

2. The rotary spray ring aromatherapy humidifier according to claim 1, wherein the rotary spray ring aromatherapy humidifier comprises an air guide frame (8) that is arranged between the air vents (22) on the intermediate frame (2).

3. The rotary spray ring aromatherapy humidifier according to claim 2, wherein the gear tray (4) is provided with second interconnecting holes (42) that are communicated with the air vents (22); and another air guide frame (8) is arranged between the second interconnecting holes (42).

4. The rotary spray ring aromatherapy humidifier according to claim 1, wherein a diameter of the limiting plate (24) is larger than a diameter of the fan blade (6), and the fan blade (6) is arranged at an inner hole of the limiting plate (24).

5. The rotary spray ring aromatherapy humidifier according to claim 1, wherein the rotary spray ring aromatherapy humidifier comprises a bearing that is arranged between an inner side of the transmission gear (31) and the limiting plate (24).

6. The rotary spray ring aromatherapy humidifier according to claim 1, wherein the driving gear (3), the transmission gear (31), and the driven gear (32) are engaged for transmission; when the driven gear (32) rotates, it drives the rotary decorative parts (5) to rotate together; and the rotary decorative parts (5) are arranged on the intermediate frame (2) in a ring shape, and the ring-spraying holes (21) are arranged at a center of the rotary decorative parts (5).

* * * * *